US006531144B2

(12) United States Patent
Kashima et al.

(10) Patent No.: US 6,531,144 B2
(45) Date of Patent: Mar. 11, 2003

(54) MICROEMULSION AEROSOL COMPOSITION

(75) Inventors: Seiichi Kashima, Takarazuka (JP); Osamu Tanaka, Habikino (JP)

(73) Assignee: Dainihon Jochugiku Co., Ltd., Osaka (JP)

( * ) Notice: Subject to any disclaimer, the term of this patent is extended or adjusted under 35 U.S.C. 154(b) by 0 days.

(21) Appl. No.: 10/200,062

(22) Filed: Jul. 22, 2002

(65) Prior Publication Data

US 2003/0026765 A1 Feb. 6, 2003

(30) Foreign Application Priority Data

Jul. 27, 2001 (JP) .................................... 2001-228366

(51) Int. Cl.[7] ........................ A01N 25/02; A01N 25/06
(52) U.S. Cl. ........................................ 424/405; 424/45
(58) Field of Search .................................. 424/45, 405

(56) References Cited

U.S. PATENT DOCUMENTS 5,603,942 A * 2/1997 Narayanan et al. ......... 424/405
5,792,465 A * 8/1998 Hagarty ...................... 424/405

* cited by examiner

*Primary Examiner*—Raymond Henley, III
(74) *Attorney, Agent, or Firm*—Nath & Associates PLLC; Gary M. Nath

(57) ABSTRACT

There is provided a microemulsion aerosol composition whose hazards of flammability and explosion are reduced and which is one-layer type and does not require to shake a container containing the composition prior to use.

A microemulsion aerosol composition containing an aerosol base solution comprising (a) an insecticidal ingredient, (b) a surfactant, (c) an aliphatic hydrocarbon having between 8 and 16 carbons, and (d) water, and (e) a liquefied petroleum gas as a propellant, wherein (b), (c) and (d) are contained in amounts of 5 to 20 vol %, 40 to 78 vol % and 15 to 53 vol %, respectively, in the aerosol base solution, and the surfactant (b) is composed of sorbitan fatty esters and polyoxyethylene polyoxypropylene alkyl ethers in a mixing ratio of 1:1 to 5:1.

4 Claims, No Drawings

MICROEMULSION AEROSOL COMPOSITION

BACKGROUND OF THE INVENTION

1. Field of the Invention

The present invention relates to an improvement of an aerosol composition containing insecticidal ingredients.

2. Description of the Related Art

Conventionally, many aqueous insecticides for application or water-based aerosols have been proposed in order to reduce the danger from fire by formulations and decrease the environmental load. However, when the formulations are prepared, aqueous organic solvent, such as alcohols are frequently used in order to attain stable emulsibility because most of the insecticidal ingredients have hydrophobic property. These formulations tend to have inferior insecticidal action on some pests to oil aerosol without water. This results from the difference in penetrability of the insecticidal ingredients from the skin surface of the pests.

The present inventors previously developed a useful aerosol composition containing an aerosol base solution comprising (a) an insecticidal ingredient, (b) a surfactant, (c) an aliphatic hydrocarbon having between 8 and 16 carbons, and (d) water, and (e) a propellant, wherein (c) and (d) are contained in specific amounts, respectively, and filed a patent application (Japanese Patent Laid-open No. 2001-89303). However, most of conventional water-based aerosols for controlling pests are emulsion formulations of water-in-oil type or oil-in-water type. And the above-mentioned useful aerosol composition is also such an emulsion formulation. Consequently, the emulsion formulations are separated into an emulsion phase and a propellant phase in the container containing them. Therefore, it is necessary to shake prior to use to disperse homogeneously the contents.

Water-based aerosols in one-layer type in which the above-mentioned problems were overcome are disclosed in Japanese Patent Publication Nos. Sho 61-45601 and Hei 7-121848. However, dimethyl ether is used as a propellant in these aerosols, and organic solvent, such as lower alcohols is further used in the latter. Therefore, these aerosols do not have sufficient performance for water-based aerosols.

SUMMARY OF THE INVENTION

Accordingly, it is an object of the present invention to provide a microemulsion aerosol composition whose hazards of flammability and explosion are reduced and which is one-layer type and therefore does not require to shake a container containing the composition prior to use.

In order to solve the above-mentioned problems, the present-inventors have carried out several researches, and found-out that compositions comprising specific surfactant, specific aliphatic hydrocarbon and water, and a propellant in specific amounts can attain the above-mentioned object, and completed the present invention.

According to a first aspect of the present invention, there is provided a microemulsion aerosol composition containing an aerosol base solution comprising (a) an insecticidal ingredient, (b) a surfactant, (c) an aliphatic hydrocarbon having 8 to 16 carbon atoms, and (d) water, and (e) a liquefied petroleum gas as a propellant, wherein (b), (c) and (d) are contained in amounts of 5 to 20 vol %, 40 to 78 vol % and 15 to 53 vol %, respectively, in the aerosol base solution, and the surfactant (b) is composed of sorbitan fatty esters and polyoxyethylene polyoxypropylene alkyl ethers in a mixing ratio of 1:1 to 5:1.

According to a second aspect of the present invention, in the microemulsion aerosol composition according to the first aspect, the surfactant (b) comprises further polyethylene glycol alkyl ethers.

According to a third aspect of the present invention, in the microemulsion aerosol composition according to the first or second aspect, the propellant (e) is contained in an amount of 40 to 70 vol % on the basis of the volume, of the microemulsion aerosol composition.

The insecticidal ingredient (a) used in the present invention includes, for example pyrethroid insecticidal ingredients, such as phenothrin, permethrin, cyphenothrin, cypermethrin, resmethrin, phthalthrin, allethrin, prallethrin, furamethrin, imiprothrin, etofenprox and the like, silicon-containing insecticidal ingredients, such as silafluofen, organophosphorus insecticides, and the like. Among them, pyrethroid insecticidal ingredients and silafluofen are preferable in the effectiveness and safety. It should be noted that when they have optical or geometrical isomers attributed to asymmetric carbons or double bonds in the chemical structure, the isomers and optional mixtures thereof may be naturally included in the scope, of the insecticidal ingredient in the present invention.

The insecticidal ingredients may be contained in an amount of 0.01–3.0 w/v % on the basis of the total volume of the microemulsion aerosol composition of the present invention. When the amount is less than 0.01 w/v %, desired effect can not be exerted. When the amount is more than 3.0 w/v %, the stability of the microemulsion is deteriorated.

The surfactant (b) in the present invention is characterized by comprising sorbitan fatty esters and polyoxyethylene polyoxypropylene alkyl ethers in a mixing ratio of 1:1 to 5:1.

The sorbitan fatty esters is exemplified by sorbitan monolaurate, sorbitan monooleate, sorbitan sesquioleate, sorbitan trioleate, sorbitan monostearate and the like. On the other hand, the polyoxyethylene polyoxypropylene alkyl ethers are exemplified by polyoxyethylene polyoxypropylene cetyl ether, polyoxyethylene polyoxypropylene lauryl ether, polyoxyethylene polyoxypropylene stearyl ether, polyoxyethylene polyoxypropylene decyltetradecyl ether, and the like.

When the mixing ratio between the sorbitan fatty esters and the polyoxyethylene polyoxypropylene alkyl ethers is out of the range of 1:1 to 5:1, microemulsion can not be formed in the aerosol or the stability of the microemulsion is deteriorated even when it is formed, therefore it is not preferable that the mixing ratio is out of the above-mentioned range.

From the viewpoint of the stability of microemulsion, it is preferable to further add polyethylene glycol alkyl esters in the surfactant having the above-mentioned formulation. The polyethylene glycol alkyl esters include for example polyethylene glycol laurate, polyethylene glycol oleate, polyethylene glycol stearate and the like to which the present invention is not limited.

The surfactant may contain other type of surfactants, such as polyoxyethylene alkyl ether, polyoxyethylene alkyl phenyl ether, polyoxyethylene styrenated phenol, the fatty ester of polyoxyethylene hardening castor oil, diglyceryl alkyl ester and the like, as far as the stability of microemulsion is not deteriorated.

It is suitable to add the surfactant as a whole in an amount of 5 to 20 vol % in the aerosol base solution in the present invention. If the amount is less than 5 vol %, suitable microemulsion can not be formed. On the other hand, if the amount is more than 20 vol %, the surfactant has an adverse effect on the insecticidal effect.

The aliphatic hydrocarbon having 8 to 16 carbon atoms (c) is added in an amount of 40 to 78 vol % in the aerosol base solution in the present invention. If the amount is less than 40 vol %, the insecticidal effect is low because the penetrability of the insecticidal ingredients from the skin surface of the pests is deteriorated. On the other hand, if the amount is more than 78 vol %, hazards of flammability are increased. The aliphatic hydrocarbon includes n-paraffins or isoparaffins, and n-paraffins are preferable in the performance. In addition, other organic solvents may be used as far as the characteristics of the present invention is not deteriorated.

In order to obtain the desired action and effect in the present invention, the mixing amount of water is set to 15 to 53 vol %. If the amount is less than 15 vol %, the problems of flammability is not overcome. On the other hand, the amount is more than 53 vol %, it is difficult to improve the insecticidal effect.

Although a liquefied petroleum gas (LPG) is used as a propellant, dimethyl ether (DME), fluoro carbon gas, compressed gas (nitrogen gas, carbon dioxide gas and the like) and the like may be mixed in a amount that a microemulsion can be formed. It is preferable to use the propellant in an amount of 40 to 70 vol % on the basis of the volume of the microemulsion aerosol composition. If the amount is less than 40 vol %, the sprayed particles become coarse, thereby causing problems in the insecticidal effect. On the other hand, the amount is more than 70 vol %, the safety against flammability is deteriorated. When the amount of the propellant is reduced or compressed gases are used, the ejection pressure is often reduced. As countermeasures therefor, it is useful to use liquefied petroleum gas with an increased ratio of propane/butane.

The present microemulsion aerosol composition may include, for example, acaricides, mildewproofing agents that are active against mold or fungi, etc., anti-fungus agents or bactericides, or synergists for pyrethroid insecticidal compounds, stabilizers, perfumes, bulking agents and the like. The acaricides include, for example, methyl 5-chloro-2-trifluoromethanesulfonamide benzoate, phenyl salicylate, 3-iodo-2-propynylbutyl carbamate and the like. The mildewproofing agents, anti-fungus agents or bactericides include, for example, 2-mercaptobenzothiazol, 2-(4-thiazolyl)benzimidazole, triforine, 3-methyl-4-isopropylphenol, ortho-phenyl phenol and the like.

DESCRIPTION OF THE PREFERRED EMBODIMENTS

Generally, the microemulsion aerosol composition of the present invention is placed in a container and used. Because the aerosol base solution in the composition is non-flammability, and the composition is one-layer type due to the mixing of propellant, the container containing the composition need not be shaken when it is used, and the microemulsion aerosol composition exerts excellent insecticidal effect against several pests. Therefore, the present invention provides extremely useful microemulsion aerosol compositions.

The microemulsion aerosol composition of the present invention is generally produced by filling an aerosol base solution into a pressure container to which a bulb portion is attached, and filling a propellant therein under pressure. The aerosol containing the composition of the present invention into a container may have a desired form of bulb, ejection hole, nozzle and the like depending on use, the purpose of use, pests to be controlled and the like. Thus, the present invention can be applied to several embodiments.

The pests to be controlled with the microemulsion aerosol composition of the present invention include, for example, Diptera pests, such as *Culex pipiens pallen, Aëdes aegypti,* Chironomidae, Muscidae (house flies), Psychodidase (moth flies), Simuliidae, Tabaninae and the like, Blattidae (cockroaches), Formicidae (ants), Diplopoda (millipedes), centipedes, Isoptera (termites) and the like, and house dust mites, such as Acaridae (acarid mites), Dermatophagoides and the like.

Consequently, the present invention provides a microemulsion aerosol composition whose hazards of flammability and explosion are reduced and which is one-layer type and therefore does not require to shake a container containing the composition prior to use.

EXAMPLES

The microemulsion aerosol of the present invention will hereinafter be described in more detail on the basis of the following concrete examples and test examples, but the present invention is not restricted to these specific examples.

Example 1

An aerosol container is filled with 120 ml of aerosol base solution comprising 0.06 g (0.02 w/v % on the basis of the volume of microemulsion aerosol composition) of d-T80-resmethrin, 0.45 g (0.15 w/v % on the basis of the volume of microemulsion aerosol composition) of d-T80-phthalthrin, 4.0 g (about 4.0 ml: 3.3 vol % in the aerosol base solution) of sorbitan monolaurate non-ionic surfactant, 3.0 g (about 3.0 ml: 2.5 vol % in the aerosol base solution) of polyoxyethylene polyoxypropylene decyltetradecyl ether non-ionic surfactant, 5.0 g (about 5.0 ml: 4.2 vol % in the aerosol base solution) of polyethylene glycol monooleate non-ionic surfactant, 86 ml (71.7 vol % in the aerosol base solution) of n-paraffin aliphatic hydrocarbon having 11–14 carbon atoms (trade name: Deotomisol) and 20 ml (16.7 vol % in the aerosol base solution) of water. Then, a bulb portion is attached to the container, and 180 ml (60 vol % on the basis of the microemulsion aerosol composition) of LPG is filled under pressure through the bulb portion into the container to obtain an aerosol containing a microemulsion aerosol composition of the present invention.

The aerosol base solution used in this example presents no flashpoint based on the method of test according to the Fire Services Act. Therefore, it is clear that the aerosol base solution in the present invention has low risk of fires. In addition, the microemulsion aerosol composition of the present invention leads to a one-layer type aerosol that a container is filled with the composition, therefore the container need not be shaken prior to use. Thus, the microemulsion aerosol is excellent in usability. Further, although it is said that aerosols containing water would exert lower insecticidal effect than oil aerosol without water, the microemulsion aerosol of the present invention has approximately identical insecticidal effect to oil aerosols containing insecticidal ingredients in the same amount.

Test Example 1

According to the procedures of Example 1, several aerosol compositions shown in Table 1 were prepared and the following tests was carried out.

(1) Stability of Microemulsion A pressure glass bottle was filled with each aerosol composition, and stored at 0°or 45° C. Thereafter, the stability of the emulsion was measured after it was stored for one month. The results are indicated as follows: a symbol "○" means that the emulsion was clear liquid and was not separated into two phases, a symbol "Δ" means that the emulsion was slightly opaque liquid and was not separated into two phases, and a symbol "×" means that the emulsion was separated into two phases.

(2) Test of Insecticidal Effect (Glass Chamber Method) After house flies (1 group: about 20 flies) were released in a glass chamber of 60 cm cubic (0.216 $m^3$), the aerosol to be tested was sprayed for 1 second, and the number of flies knocked down was observed with the time elapsed. The value of $KT_{50}$ is calculated from the results, and the relative effect based on the effect of an oil aerosol defined as 1.0 is shown in Table 1.

(3) Flammability of Base Solution The flammability of each aerosol base solution was measured with Cleveland open-cup flashpoint tester. When a flashpoint was measured, the base solution is indicated as the symbol "+". On the other hand, when no flashpoint was measured, the base solution was indicated as the symbol "–".

TABLE 1

| | Aerosol base solution*1 | | | | | | | | |
|---|---|---|---|---|---|---|---|---|---|
| Sample No. | Insecticidal Ingredient | Surfactant*3 | Aliphatic Hydrocarbon | Water | Propel-lant*1 | Stability 0° C. | Stability 45° C. | RE*2 | Inflam-mability |
| Present Invention | | | | | | | | | |
| 1 | Resmethrin 0.02 Phthalthrin 0.15 | A 4.7 B 2.5 C 5.0 | n-paraffin 69 | 17 | LPG 60 | ○ | ○ | 0.92 | – |
| 2 | Imiprothrin 0.1 Phenothrin 0.3 | D 5.2 E 2.0 F 4.8 | iso-paraffin 58 | 26 | LPG 50 DME 5 | ○ | ○ | 0.93 | – |
| 3 | Silafluofen 0.2 Phenothrin 0.1 | A 6.3 B 3.6 | n-paraffin 71 | 18 | LPG 56 | Δ | ○ | 0.90 | – |
| Comparative Example | | | | | | | | | |
| 1 | Resmethrin 0.02 Phthalthrin 0.15 | A 4.7 C 5.0 | n-paraffin 69 | 19 | LPG 60 | X | X | 0.72 | – |
| 2 | Resmethrin 0.02 Phthalthrin 0.15 | B 3.6 C 5.0 | n-paraffin 69 | 20 | LPG 60 | X | X | 0.78 | – |
| 3 | Resmethrin 0.02 Phthalthrin 0.15 | A 3.4 B 5.1 | n-paraffin 69 | 20 | LPG 60 | X | X | 0.81 | – |
| 4 | Resmethrin 0.02 Phthalthrin 0.15 | A 8.5 B 1.0 | n-paraffin 69 | 19 | LPG 60 | X | X | 0.76 | – |
| 5 | Resmethrin 0.02 Phthalthrin 0.15 | A 15.8 B 7.5 | n-paraffin 47 | 28 | LPG 60 | Δ | ○ | 0.68 | – |
| 6 | Resmethrin 0.02 Phthalthrin 0.15 | A 6.3 B 3.6 | n-paraffin 80 | 9 | LPG 60 | ○ | Δ | 0.84 | + |
| 7 | Resmethrin 0.02 Phthalthrin 0.15 | A 6.3 C 3.6 | n-paraffin 71 | 18 | DME 56 | Δ | Δ | 0.65 | – |
| 8 | Resmethrin 0.02 Phthalthrin 0.15 | G 4.5 C 5.0 | n-paraffin 76 | 18 | LPG 50 | — | — | 0.91 | – |

TABLE 1-continued

| Sample No. | Aerosol base solution*1 Insecticidal Ingredient | Surfactant*3 | Aliphatic Hydrocarbon | Water | Propellant*1 | Stability 0° C. | 45° C. | RE*2 | Inflammability |
|---|---|---|---|---|---|---|---|---|---|
| 9 | Resmethrin 0.02 Phthalthrin 0.15 | H 0.9 I 0.3 C 0.3 | — | 97 | DME 33 | ○ | ○ | 0.47 | – |

*1The amount of each component is indicated by the following unit:
Insecticidal ingredient: w/v % in the microemulsion aerosol; surfactant, aliphatic hydrocarbon and water: vol % in the aerosol base solution; Propellant: vol % in the microemulsion aerosol.
*2"RE" means relative insecticidal effect.
*3Surfactants used in this example are as follows:
A: Sorbitan monolaurate; B: Polyoxyethylene polyoxypropylene decylteradecyl ether; C: Polyethylene glycol monooleate; D: Sorbitan monostearate; E: Polyoxyethylene polyoxypropylene lauryl ether; F: Polyethylene glycol monolaurate; G: Sorbitan sesquioleate; H: Polyoxyethylene polyoxypropylene cetyl ether; I: Polyoxyethylene polypropylene glycol monooleate.

From the results shown in Table 1, it is clear that the aerosol base solution constituting the microemulsion aerosol composition of the present invention corresponds to a non-hazardous material based on the Fire Services Act and that the microemulsion aerosol composition of the present invention is greatly reduced in hazards of flammability. In addition, the composition is one-layer type and excellent in the stability. Further, the composition is approximately equal in the insecticidal effect to oil aerosols as control, therefore it is extremely useful.

On the other hand, comparative examples 1 and 2 do not contain surfactant composed of sorbitan fatty esters and polyoxyethylene polyoxypropylene alkyl ethers, comparative examples 3 to 5 have a mixing ratio of the two components that does not range in 1:1 to 5:1 or contain more than 20 vol % of surfactant based on the aerosol base solution. These comparative examples are low in the stability or insecticidal effect. Comparative example 6 contains more than 78% of aliphatic hydrocarbon and small quantity of water, therefore it has a problem in the flammability. When DME is used as a propellant (comparative example 7), it is low in the stability of microemulsion or insecticidal effect. Further, conventional water-based aerosol composition, such as comparative example 8 disclosed in Japanese Patent Laid-open No. 2001-89303 is two-pack type and need be shaken prior to use. The formulation in which the surfactant disclosed in Japanese Patent Publication No. Sho 61-45601 is used is deficient in the insecticidal effect.

What is claimed is:

1. A microemulsion aerosol composition containing an aerosol base solution comprising (a) an insecticidal ingredient, (b) a surfactant, (c) an aliphatic hydrocarbon having 8 and 16 carbon atoms, and (d) water, and (e) a liquefied petroleum gas as a propellant, wherein (b), (c) and (d) are contained in amounts of 5 to 20 vol %, 40 to 78 vol % and 15 to 53 vol %, respectively, in the aerosol base solution, and the surfactant (b) is composed of sorbitan fatty esters and polyoxyethylene polyoxypropylene alkyl ethers in a mixing ratio of 1:1 to 5:1.

2. A microemulsion aerosol composition according to claim 1, wherein the surfactant (b) comprises further polyethylene glycol alkyl esters.

3. A microemulsion aerosol composition according to claim 1, wherein the propellant (e) is contained in an amount of 40 to 70 vol % on the basis of the volume of the microemulsion aerosol composition.

4. A microemulsion aerosol composition according to claim 2, wherein the propellant (e) is contained in an amount of 40 to 70 vol % on the basis of the volume of the microemulsion aerosol composition.

* * * * *